United States Patent
Berthiaume et al.

(10) Patent No.: US 6,180,117 B1
(45) Date of Patent: Jan. 30, 2001

(54) METHOD OF PREPARING MICROEMULSIONS OF AMINO SILICONE FLUIDS AND MQ RESIN MIXTURES

(75) Inventors: Marianne D. Berthiaume, Latham; James H. Merrifield, Ballston Spa; Donna A. Riccio, Watervliet, all of NY (US)

(73) Assignee: General Electric Company, Pittsfield, MA (US)

( * ) Notice: Under 35 U.S.C. 154(b), the term of this patent shall be extended for 0 days.

(21) Appl. No.: 08/385,293

(22) Filed: Feb. 10, 1995

Related U.S. Application Data

(63) Continuation-in-part of application No. 08/321,640, filed on Oct. 11, 1994, now Pat. No. 5,578,298, which is a continuation-in-part of application No. 08/250,124, filed on May 27, 1994, now Pat. No. 5,683,625.

(51) Int. Cl.[7] .............................. A61K 7/075; A61K 7/09; A61K 7/11; B01F 3/08
(52) U.S. Cl. ................ 424/401; 424/70.12; 424/70.121; 424/70.122; 424/70.13; 514/938; 514/975; 516/76; 516/925; 516/928
(58) Field of Search ..................................... 252/312, 314; 424/70.122, 70.13, DIG. 2, 70.12, 70.121, 401; 514/938, 975; 106/287.11; 516/76, 925, 928

(56) References Cited

U.S. PATENT DOCUMENTS

| | | | |
|---|---|---|---|
| 2,750,947 | * 6/1956 | Gant | 132/206 |
| 3,772,247 | 11/1973 | Flannigan | 528/31 |
| 4,247,330 | 1/1981 | Sanders, Jr. | 106/287.11 X |
| 4,620,878 | 11/1986 | Gee | 106/287.15 |
| 4,774,310 | 9/1988 | Butler | 528/23 |
| 4,782,095 | 11/1988 | Gum | 514/937 |
| 4,797,272 | 1/1989 | Linn et al. | 424/59 |
| 4,801,447 | 1/1989 | Gum | 424/68 |
| 4,839,167 | * 6/1989 | Yamamoto et al. | 424/DIG. 2 |
| 5,057,572 | 10/1991 | Chrobaczek et al. | 524/588 |
| 5,234,495 | 8/1993 | Breneman et al. | 106/287.1 |
| 5,244,598 | * 9/1993 | Merrifield et al. | 252/314 |
| 5,334,737 | 8/1994 | Thimineur et al. | 556/440 |
| 5,439,673 | * 8/1995 | Murray | 424/70.12 |

FOREIGN PATENT DOCUMENTS

| | | |
|---|---|---|
| 0 138 192 | 4/1985 | (EP) . |
| 0138192 | 4/1985 | (EP) . |
| 0358652 | 3/1990 | (EP) . |
| 0 404 027 | 12/1990 | (EP) . |
| 0460683 | 12/1991 | (EP) . |
| 0 479 000 | 4/1992 | (EP) . |
| 0 532 256 | 3/1993 | (EP) . |
| 2 624 867 | 12/1988 | (FR) . |
| 2 079 300 | 1/1982 | (GB) . |
| 2079300 | 1/1982 | (GB) . |
| 2215729 | 9/1989 | (GB) . |
| WO/88 08436 | 4/1988 | (WO) . |

* cited by examiner

Primary Examiner—Richard D. Lovering
(74) Attorney, Agent, or Firm—Kenneth S. Wheelock

(57) ABSTRACT

Microemulsion compositions comprising MQ resins and microemulsifiable amino silicone fluids or gums and a surfactant having a high phase inversion temperature, the microemulsions formed therewith, a means for preparing said microemulsions, and personal care products comprising said microemulsions.

13 Claims, No Drawings

US 6,180,117 B1

METHOD OF PREPARING MICROEMULSIONS OF AMINO SILICONE FLUIDS AND MQ RESIN MIXTURES

CROSS-REFERENCE TO RELATED APPLICATIONS

This application is a continuation-in-part of U.S. Ser. No. 08/321,640 filed Oct. 11, 1994, now U.S. Pat. No. 5,578, 298, which is a continuation-in-part of U.S. Ser. No. 08/250, 124 filed May 27, 1994 and now U.S. Pat. No. 5,683,625.

FIELD OF THE INVENTION

The instant invention comprises a method for preparing microemulsions. The process of the invention comprises blending an amino silicone fluid MQ resin mixture with a surfactant having a high phase inversion temperature adding an approximately equal amount of water at a temperature approximately equal to the phase inversion temperature of the surfactant, acidifying, followed by rapidly adding water. The instant invention further comprises personal care products comprising the microemulsion prepared by the process of the invention.

BACKGROUND OF THE INVENTION

The instant invention is related to a method of making microemulsion blends having an average particle size of from about 0.001 microns to about 0.05 microns whereby the blend comprises at least one of a low amino content silicone, a resin or an MQ resin and a surfactant having a high phase inversion temperature. The instant invention is further related to personal care products comprising said microemulsions.

Microemulsions containing silicone fluids have been found to be useful in a variety of personal care products. As defined herein, the term "microemulsions" refers to transparent, mechanically and thermally stable systems comprising small droplets having a mean or average particle diameter usually not more than 0.05 microns in diameter, preferably not more than 0.040 microns in diameter and most preferably not more than 0.025 microns in diameter. The small size of the droplets imparts a high degree of transparency to the emulsion.

The use of microemulsions is known in the art, see for example U.S. Pat. Nos. 4,797,272 (Linn et al.) and 4,620, 878 (Gee). U.S. Pat. No. 4,797,272 to Linn et al. discloses water-in-oil microemulsion compositions having a mean droplet size ranging from about 0.001 microns to about 0.200 microns. U.S. Pat. No. 4,620,878 to Gee discloses a polyorganosiloxane emulsion that contains a polyorganosiloxane containing at least one polar radical such as an amino or ammonium radical attached to the silicon of the siloxane by Si—C or Si—O—C bonds or at least one silanol radical and at least one surfactant that is insoluble in the polyorganosiloxane. Water is added forming a translucent oil concentrate. The translucent oil concentrate is then rapidly dispersed in water to prepare emulsions with fairly low particle sizes. A drawback of Gee's teachings is that the oil concentrate must be diluted with very large quantities of water such that the final emulsion rarely contains more than about 5 wt. % silicone solids. The emulsions prepared by Gee typically have an average particle size of less than 0.14 microns.

Microemulsions of volatile silicones are taught in the art, for example U.S. Pat. Nos. 4,782,095 and 4,801,447, however these microemulsions have required large amounts of surfactants. The high levels of surfactants required in the prior art applications are detrimental in many applications.

Chrobaczek and Tschida in U.S. Pat. No. 5,057,572 teach the preparation of an aminoalkyl substituted polysiloxane where the silicone fluid, a water-soluble emulsifier, in contrast to Gee, water and an acid are combined and heated to 50° C. The necessity for a specific sequence of process steps, such as order of addition, is not taught by Chrobaczek. While Chrobaczek teaches this procedure is applicable to silicone fluids with an amino content of 0.1 meq./gr., in practice microemulsions result only when the amino content is above a threshold of about 0.12 to 0.14 meq./gr. Below this threshold level the particle size of the emulsion is such that the emulsion is hazy, and therefore not a true microemulsion, true microemulsions possess optical transparency to a greater or lesser degree, as measured by an ASTM haze number of less than about 150.

Breneman et al. in U.S. Pat. No. 5,234,495 teach the preparation of microemulsions through a process utilizing the blending of an organo modified polysiloxane, e.g. an aminofunctional polysiloxane, an organo modified polysiloxane emulsifier, water, and an alkaline metal salt Heating such a blend above the cloud point of the mixture and simultaneously subjecting the mixture to high shear mixing produces a liquid phase that can be cooled to form a microemulsion.

Microemulsions of aminofunctional silicones, particularly high viscosity aminofunctional silicone fluids or gums, provide beneficial results when used in personal care product formulations. Further MQ resins impart desirable properties to personal care products. Similarly methods of incorporating MQ resins into personal care products and preparing microemulsions of MQ resins are desirable. It continues to be desirable to provide alternative or improved methods for preparing microemulsions of small average particle size.

SUMMARY OF THE INVENTION

In one embodiment, the instant invention comprises a transparent oil-in-water microemulsion comprising: (a) a microemulsifiable amino silicone fluid or gum, (b) an MQ (or alternatively a siloxysilicate) resin or mixture thereof, (c) a surfactant having a high phase inversion temperature, and (d) water.

In another aspect, the instant invention provides a method of preparing a transparent polyorganosiloxane microemulsion having a mean particle size of from about 0.001 to about 0.050 microns, preferably from about 0.010 to about 0.030 microns, and most preferably from about 0.010 to about 0.025 microns, comprising a microemulsifiable high viscosity amino silicone fluid or gum and at least one surfactant having a high phase inversion temperature.

Other aspects of the invention are microemulsions of polydimethylsiloxane MQ resin mixtures and personal care products comprising the microemulsions of the present invention.

DETAILED DESCRIPTION OF THE INVENTION

The instant invention is based upon the discovery that functionalized silicones such as amino functional silicone fluids or gums are capable of forming microemulsions and may be blended with surfactants having a high phase inversion temperature and the blend processed such that the mixture forms a microemulsion. It has been discovered that when blended with other resins, particularly MQ resins, that the amino functional silicone MQ resin blend may be microemulsified. Such microemulsions are generally transparent or translucent. By transparent applicants mean the absence of turbidity or haze wherein haze is defined by an ASTM test, specifically ASTM test number D871 using turbidity suspension standards and wherein said haze or turbidity is below an upper limit of about 150. At levels of the haze number above about 50 the microemulsions of the present invention begin to gradually change from transparent to translucent. The haze numbers of the microemulsions of the present invention range from 0 to about 150, more preferably from about 0 to about 80 and most preferably from 0 to about 50. The turbidity suspension standards used in the ASTM test D871 are available from Hellige Incorporated of Garden City, N.Y. Applicants note that pure distilled water is 0 on the haze scale.

Polyorganosiloxane microemulsions prepared by the method of the instant invention have a mean particle size of from about 0.005 to about 0.050 microns, preferably from about 0.010 to about 0.030 microns, and most preferably from about 0.010 to about 0.025 microns. Generally haze and average particle size correlate with one another but they are also affected by the relative amounts of the three major components of the emulsion, the silicone oil or mixtures thereof, the emulsifier and the water. Thus while at a constant oil to water ratio the haze and average particle size might correlate, haze by itself is not both a necessary and sufficient criterion to be an indicator of average particle size in a microemulsion unless other constraints are specified.

By microemulsifiable applicants define the term to mean capable of forming a microemulsion wherein the mean particle size of the emulsion ranges from 0.0001 microns to about 0.050 microns. By microemulsifiable silicone applicants define a silicone or a mixture of silicones that can form a microemulsion as defined by applicants herein before.

The phase inversion temperature is that temperature at which a given surfactant is equally soluble in a lipophilic and a hydrophilic phase that are coextensive. Generally the hydrophilic phase of interest or use is water. At the phase inversion temperature, the surfactant, the hydrophilic phase and the lipophilic phase are in a thermodynamic state of minimum free energy. This thermodynamic state is characterized by a minimum in particle size of the emulsion formed therewith when the mixture is emulsified. Thus the phase inversion temperature has a tendency to be specific for a given composition of components. While the phase inversion temperature varies as a function of composition, when one of the two liquid phases is held constant e.g. water, the phase inversion temperature of a series of mixtures utilizing a given surfactant, water, and a variety of lipophilic phases that are immiscible with the water, the phase inversion temperature will tend to vary over a much narrower range of temperatures.

In one embodiment of the instant invention an oil-resin-surfactant mixture is prepared by blending:

(1) an amount ranging from 1 to 40, more preferably 5 to 40, and most preferably from 10 to 30 parts per hundred of the final composition of the microemulsion of a polyorganosiloxane that can be microemulsified, A(1), optionally having an amino content of from about 0.10 to about 3.0 milliequivalents per gram and comprising one or more silicones of the formula:

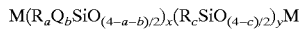

whereby in the formulas above R is a hydrocarbon or hydrocarbon radical having from 1 to about 6 carbon atoms, Q is a polar radical having the general formula—$R^1HZ$, wherein $R^1$ is a divalent linking group bound to hydrogen and the radical Z, comprised of carbon and hydrogen atoms; carbon, hydrogen and oxygen atoms, or carbon, hydrogen and nitrogen atoms; and Z is an organic amino functional radical containing at least one amino functionality; "a" assumes values ranging from about 0 to about 2, "b" assumes values ranging from about 1 to about 3, "a"+"b" is less than or equal to 3, and "c" is a number in the range of from about 1 to about 3; and x is a number in the range of from 1 to about 2,000 preferably from about 3 to about 50 and most preferably from about 3 to about 25, and y is a number in the range of from about 80 to about 10,000, preferably from about 125 to about 10,000, and most preferably from about 150 to about 1,000, and M is any suitable silicone endstopping group known in the art, preferably trimethylsiloxy. Non-limiting examples of radicals represented by R include alkyl radicals such as methyl, ethyl, propyl, isopropyl, butyl, isobutyl, amyl, isoamyl, hexyl, isohexyl, and the like; alkenyl radicals such as vinyl, halo vinyl, alkyl vinyl, allyl, haloallyl, alkylallyl, cycloalkyl radicals such as cyclobutyl, cyclopentyl, cyclohexyl and the like, phenyl radicals, benzyl radicals, halohydrocarbon radicals such as 3-chloropropyl, 4-bromobutyl, 3,3,3-trifluoropropyl, chlorocyclohexyl, bromophenyl, chlorophenyl and the like, and sulfur containing radicals such as mercaptoethyl, mercaptopropyl, mercaptohexyl, mercaptophenyl and the like; preferably R is an alkyl radical containing from 1 to about 6 carbon atoms; and most preferably R is methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, $OH_2CH_2$—, —$OCH_2CH_2CH_2$—,—$CH_2CH(CH_3)C(O)OCH_2$,—$(CH_2)_3$ $CC(O)OCH_2CH_2$—, —$C_6H_4C_6H_4$—, —$C_6H_4CH_2C_6H_4$—, and —$(CH_2)_3C(O)SCH_2CH_2$—.

Z is an organic amino functional radical containing at least one amino functionality. One possible formula for Z is —$NH(CH_2)_zNH_2$ where z is one or greater. Another possible formula for Z is —$N(CH_2)_z(CH_2)_{zz}NH$ where both z and zz are independently one or greater, this structure encompasses diamino ring structures such as piperazinyl. Z is most preferably a —$NHCH_2CH_2NH_2$ radical. Another possible formula for Z is —$N(CH_2)_z(CH_2)_{zz}NX_2$ or $NX_2$ wherein each X of $X_2$ is independently selected from the group consisting of hydrogen and 1 to 12 carbon atom alkyl groups and zz is zero.

Q is most preferably an amine functional polar radical having the formula —$CH_2CH_2CH_2NHCH_2CH_2NH_2$.

In the formulas, "a" assumes values ranging from about 0 to about 2, "b" assumes values ranging from about 1 to about 3, "a"+"b" is less than or equal to 3, and "c" is a number in the range of from about 1 to about 3. The molar ratio of $R_aQ_bSiO_{(4-a-b)/2}$ units to $R_cSiO_{(4-c)/2}$ units ranges from about 1:2 to about 1:65, preferably from about 1:5 to about 1:65, and most preferably from about 1:15 to about 1:20. When one or more silicones of the above formula are used, it is to be understood that the variously variable substituents in the above formula may be different among the varying silicone components comprising the silicone mixture.

It is preferred to use amino functional silicone gums or fluids A(1) in the instant invention having the formula:

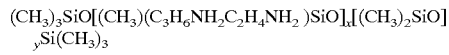

wherein x is a number in the range of from 1 to about 2,000 preferably from about 3 to about 50 and most preferably from about 3 to about 25, and y is a number in the range of from about 80 to about 10,000, preferably from about 125 to about 10,000, and most preferably from about 150 to about 1,000, wherein said amino functional silicone fluid or gum has a viscosity ranging from 100 to 10,000,000 centistokes at 25° C., preferably the viscosity ranges from 200 to 20,000 centistokes, and most preferably the viscosity ranges from 500 to 5,000 centistokes.

(2) additionally blending an amount ranging from 10 to 30 parts per hundred of the final composition of the microemulsion of an MQ resin, A(2), having the general formula:

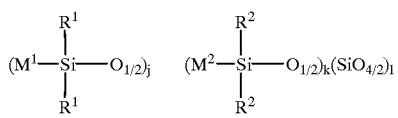

(1)

where both $R^1$ and $R^2$ may be an alkyl group having from 1 to 12 carbon atoms, and both $M^1$ and $M^2$ may independently be phenyl, phenethyl, polyether, hydrogen, or 1 to 23 carbon atom alkyl in any combination subject to the limitation that the ratio of the subscripts j, k, and l satisfies the following relationship:

$$0.5 \leq (j+k)/l \leq 4.0. \qquad (2)$$

The MQ resin itself is a polymer composed of a distribution of exemplary species having a range of molecular weights. The MQ resin can be defined in a specific instance by setting the value for l equal to unity. Thus, when l=1, j ranges from between 0 and 4, and k ranges from between 0 and 4. Due to the restrictions of chemical stoichiometry when l=1, j+k=4. It is also preferred that the ratio of (j+k)/l be equal to about 2. The relationship of equation 2) is subject to the further constraint that j+k must be at least one. A preferred resin is satisfied by the following values for the subscripts j, k, and l; j=2, k=0, and l=1 when $R^1=CH_3$.

When $M_1$ and/or $M_2$ is a polyether, the polyether has the general formula:

where $R^3$ is $—(CH_2)_n—$ with n ranging from 1 to about 20, $R^4$ is a one to twenty carbon alkyl group, and $R^5$ is selected from the group consisting of H, $—CH_3$, and $—C(O)CH_3$; and where u and v are integers ranging from 0 to 20 subject to the limitation that u+v≧1. It is to be noted that the MQ resins utilized in the microemulsion compositions of the present invention, the process of manufacturing the microemulsions of the present invention and cosmetic formulations utilizing the microemulsions of the present invention have viscosities ranging from 50 to 5,000, preferably 50 to 3,000 and most preferably from 100 to 2,000 centistokes at 25° C.

(3) adding to the silicone blend from steps (1) and (2), of from about 1 to 30 parts per hundred of the final composition of the microemulsion of at least one surfactant, A(4), wherein at least one of the surfactants has a high phase inversion temperature, said phase inversion temperature generally ranging from about 45 to about 95° C.;

(4) heating the blend of silicone(s) and surfactant(s) to a temperature ranging from about 45° C. to about 95° C., which is a temperature below the phase inversion temperature of the surfactant(s), while stirring;

(5) water, Part I water in the examples, in an amount equal in weight to the weight of the silicone(s) used in Part I added slowly;

(6) adding an amount of an acid such that the final pH of the microemulsion is between about 4 and 7; preferably steps (5) and (6) are accomplished simultaneously either by the separate addition of water and a suitable acid or by the addition of an aqueous solution of a suitable acid. A preferred acid is acetic acid, however other acids may also be used such as HCl, hypophosphorous, lactic, propionic, glycolic, formic, and nitric.

(7) water, Part II water in the examples, in an amount ranging from 40 to about 90 parts, said part II water having a temperature ranging from 0° C. to about 95° C. below the temperature of acidified emulsion such that by the addition of said cold water the temperature of said microemulsion is cooled rapidly. Additionally, Part II water may contain a high molecular weight polymer such as polyvinyl alcohol, hydroxy methylcellulose or the like, to improve the stability of the final emulsion.

A(4) contains at least one surfactant, wherein at least one of the surfactants has a phase inversion temperature ranging from 50° C. to about 95° C., said surfactant hereinafter referred to as the primary surfactant. Other optional surfactants are referred to as secondary surfactants.

The surfactant or blend of surfactants has a hydrophilic-lipophilic balance value of from about 10 to about 16, preferably from about 11 to about 16, and most preferably from about 12 to about 13. The preferred hydrophilic-lipophilic balance value may vary as a consequence of increasing the level of volatile silicone in the microemulsifiable silicone.

The primary surfactant may be cationic, anionic, nonionic or amphoteric in nature. Examples of such surfactants are disclosed in U.S. Pat. No. 4,620,878 to Gee which is hereby incorporated by reference. Generally, nonionic surfactants are preferred for use in the instant invention.

Surfactants useful as the primary surfactant in the instant invention include the polyoxyethylene sorbitan esters of $C_{10}$ to $C_{22}$ fatty acids having up to 95% ethylene oxide; polyoxyethylene sorbitol esters of $C_{10}$ to $C_{22}$ fatty acids, polyoxyethylene derivatives of fatty phenols having 6 to carbon atoms up to 95% ethylene oxide; fatty amino and amido betaines having 10 to 22 carbon atoms, and polyethylene condensates of $C_{10}$ to $C_{22}$ fatty acids or fatty alcohols having up to 95% ethylene oxide.

Preferred primary surfactants for the practice of the instant invention include, but are not limited to, the alkylphenoxy polyethoxy ethanols, which are nonionic surfactants possessing varying amounts of ethylene oxide units and are available from Union Carbide Corporation under the general TRITON® trade name; trimethylnonyl polyethylene glycol ethers and polyethylene glycol ethers of 11–15 carbon atom containing alcohols, which may be linear or branched, preferably branched, available from Union Carbide Corporation under the general trade name TERGITOL®; the nonionic ethoxylated tridecyl ethers, available from Emery Industries under the trade name TRYCOL®.

The preferred surfactants for use as the primary surfactant of the instant invention are the trimethylnonyl polyethylene glycol ethers and polyethylene glycol ethers of 11–15 carbon atom containing alcohols, which may be linear or branched, preferably branched, available from Union Carbide Corporation under the trade name TERGITOL®. A preferred surfactant for use as the primary surfactant of the instant invention is a trimethylnonyl polyethylene glycol ether. The most preferred primary surfactant is 2,6,8-trimethyl-4-nonyloxypolyethylene oxide (TERGITOL® TMN-6)

The optional secondary surfactants may be anionic, cationic, nonionic, or amphoteric and may either be soluble or insoluble in the preferred amino functional silicone of A(1). Nonionic surfactants are preferred. Non-limiting examples of surfactants that are soluble in the amino functional silicone include the alkyl phenol ethoxylates. A particularly preferred optional secondary surfactant is TRITON X405®.

Preferably, the optional secondary surfactant used in this invention is also insoluble in the silicone of A(1). The preferred surfactants for use as the secondary surfactants in the instant invention are the alkyl phenoxy polyethoxy ethanols.

The amount of A(4) is in the range of from about 1 to about 30, preferably from about 1 to about 20, and most preferably from about 5 to about 15, parts by weight per 100 parts by weight of the final microemulsion composition.

The blend of silicones, surfactants and water is homogenized in a homogenizer or other suitable mixing equipment. The length of time necessary to form a homogeneous mixture or emulsion in this step will depend on mixing equipment parameters and can be determined by those skilled in the art without undue experimentation. High shear mixing, either at ambient pressure or under conditions where the reaction medium is pressurized are generally unnecessary in order to form the microemulsions of the instant invention. Because the blend contains a surfactant having a high phase inversion temperature, the temperature at which the microemulsion is formed must be carefully controlled. Thus the step of adding part I water is performed in a temperature range varying between 45° C. and 95° C., more preferably varying between 55° C. and 90° C., and most preferably varying between 65° C. and 85° C.

In step (6) the microemulsion is acidified to bring the pH of the emulsion into a range varying between 4 and 7, more preferably between 5 and 6.5, and most preferably between 5.5 and 6.5. This step is particularly effective when combined with step (5).

In order to change the pH of the reaction medium, it is necessary to consider the quantity of amino functional silicone or silicone present in the reaction mixture. The amount of acid needed to provide such pH values will depend on the amount of the amino functional silicone or silicone fluid A(1) and the amino content of the amino functional silicone fluid. For example, with the amino functional silicone fluid having an amino content of 0.6 milliequivalents per gram, the amount of acid sufficient to provide a pH within the desired range will be approximately 2.5 parts per weight per 100 parts per weight of the amino functional silicone fluid. With an amino functional silicone fluid having an amino content of 3.0 milliequivalents per gram, the weight of acid will be about 1.25 parts per weight per 100 parts per weight of the fluid. While the weights of acid necessary to achieve a given pH may vary depending on the molecular and equivalent weights of the acid chosen to control the pH, control of pH to the desired value is the primary purpose of the acid addition. Further, it has been found that the addition of acid must be simultaneous with the addition of the part I water.

The amino functional silicone microemulsions of the present invention are useful in a variety of personal care product applications such as hair conditioners, the so-called 2-in-1 shampoos, and hair fixative preparations such as styling gels mousses and the like. For purposes of personal care applications the conditioner formulations generally comprise an amino functional silicone microemulsion content ranging from about 1 weight percent to about 20 weight percent, more preferably from about 5 weight percent to about 10 weight percent, and most preferably from about 6 weight percent to about 7 weight percent For purposes of personal care applications the 2-in-1 shampoo formulations generally comprise an amino functional silicone microemulsion content ranging from about 0.5 weight percent to about 10 weight percent, more preferably from about 1 weight percent to about 5 weight percent, and most preferably from about 3 weight percent to about 4 weight percent For purposes of personal care applications the fixative formulations generally comprise an amino functional silicone microemulsion content ranging from about 0.5 weight percent to about 10 weight percent, more preferably from about 2 weight percent to about 6 weight percent, and most preferably from about 3 weight percent to about 5 weight percent. The personal care products utilizing microemulsions prepared by the process of the instant invention will typically exhibit haze numbers below about 100. Applicants note that the weight percent ranges herein before described constitute weight percent ranges for the finished microemulsions as a component of the personal care product Thus a microemulsion prepared by the process of the present invention will have a silicone content varying from about 0.5 weight percent to about 25 weight percent, which will vary from about 0.1 weight percent to about 7 weight percent as a percentage of the final composition of the personal care product when the microemulsion is incorporated into the personal care product Additionally, the microemulsions of the present invention may be formulated into textile treating products or skin care formulations including color cosmetics.

All of the U.S. patents referred to herein are herewith specifically incorporated by reference.

EXPERIMENTAL

The procedure outlined in the detailed description of the invention was utilized to prepare the following non-limiting examples, examples 1 through 24, which are illustrative of the microemulsions of the instant invention. Uses of these microemulsions in personal care products are also demonstrated. Examples 39 through 43 are illustrative of personal care formulations.

Example 1

While warming to 70° C., 16 parts of an aminofunctional silicone (linear, trimethylsilyl terminated, —$(CH_2)_3$—NH—$CH_2$—$CH_2$—$NH_2$, viscosity of 150 to 400 centistokes, amine content of 0.12 meq/gr.) was mixed with 8 parts TERGITOL TMN-6. Part I water (16 parts) was then added dropwise at 70° C. After water addition was complete, 1 part of acetic acid was added. The mixture thickened and became translucent Part II water (58 parts) was then added rapidly with good agitation. Upon cooling, a microemulsion having an ATM haze number of about 40 was obtained.

Comparative Example 1

This example was prepared in the same fashion as Example 6 in U.S. Pat. No. 5,057,572. While warming to 70° C., 16 parts of an aminofunctional silicone (linear, trimethylsilyl terminated, —$(CH_2)_3$—NH—$CH_2$—$CH_2$—$NH_2$, viscosity of 150 to 400 centistokes, amine content of 0.12 meq/gr.) was mixed with 8 parts TERGITOL TMN-6 and 74 parts water to form a homogeneous mixture. Lactic acid (1 part) was then added at 70° C. After cooling a milky emulsion was obtained. The haze number of this preparation was greater than 200.

Example 2

This example shows the effect of adding part II water slowly. While warming at 70° C., 20 parts of an aminofunctional silicone (linear, trimethylsilyl terminated, —$(CH_2)_3$—$NHCH_2$ $CH_2$—$NH_2$, viscosity of 150 to 400 centistokes, amine content of 0.12 meq/gr.) was mixed with 12.5 parts TERGITOL TMN-6. Part I water was then added dropwise at 70° C. After water addition was complete, 0.5 parts of acetic acid was added. The mixture thickened and became translucent Part II water (53 parts) was then added dropwise with good agitation. The mixture slowly became thicker and then eventually thinned out towards the end of the water addition. Upon cooling, a microemulsion with a haze of about 200 was obtained.

Examples 3–7

These examples show the effect of different amounts of part I water (the amounts specified are in grams):

| Component | Ex. 3 | Ex. 4 | Ex. 5 | Ex. 6 | Ex. 7 |
|---|---|---|---|---|---|
| Amino fluid A1 | 65 | 65 | 65 | 65 | 65 |
| TERGITOL TMN-6 | 40 | 40 | 40 | 40 | 40 |
| Part I Water | 40 | 65 | 90 | 120 | 220 |
| Acetic Acid | 1 | 1 | 1 | 1 | 1 |
| Part II Water | 180 | 155 | 1130 | 100 | 0 |
| Haze | 150 | 30 | 90 | 200+ | 200+ |
| pH | 5.5 | 5.5 | 5.5 | 5.5 | nm |

Examples 8–12

These examples show the effect of different amounts of surfactant (the amounts specified are in grams):

| Component | Ex. 8 | Ex. 9 | Ex. 10 | Ex. 11 | Ex. 12 |
|---|---|---|---|---|---|
| Amino fluid A1 | 65 | 65 | 65 | 65 | 65 |
| TERGITOL TMN-6 | 65 | 40 | 20 | 45 | 27.5 |
| Part I Water | 65 | 65 | 65 | 65 | 65 |
| Acetic Acid | 1 | 1 | 1 | 1 | 1 |
| Part II Water | 130 | 155 | 175 | 150 | 167.5 |
| Haze | 100 | 40 | 200 | 80 | 100 |
| pH | 5.5 | 5.5 | 5.5 | 5.5 | 5.5 |

Examples 13–17

These examples show the effect of different temperatures of part II water and of using different amino fluids (the amounts specified are in grams):

| Component | Ex. 13 | Ex. 14 | Ex. 15 | Ex. 16 | Ex. 17 |
|---|---|---|---|---|---|
| Amino fluid A1 | 65 | 65 | 65 | 0 | 0 |
| Amino fluid A2 | 0 | 0 | 0 | 65 | 65 |
| TERGITOL TMN-6 | 40 | 40 | 40 | 40 | 40 |
| Part I Water | 65 | 65 | 65 | 65 | 65 |
| Acetic Acid | 1 | 1 | 1 | 1 | 1 |
| Part II Water | 155 | 155 | 115 | 155 | 0 |
| Part II water Temperature ° C. | 25 | 0 | 75 | 25 | 25 |
| Haze | 40 | 50 | 50 | 15 | 30 |
| pH | 5.5 | 5.5 | 5.5 | 5.5 | nm |

Examples 18–24

These examples show the effect of using fluids with different amine concentrations at a low amino content (the amounts specified are in grams):

| Component | Ex. 18 | Ex. 19 | Ex. 20 | Ex. 21 | Ex. 22 | Ex. 23 | Ex. 24 |
|---|---|---|---|---|---|---|---|
| Amino fluid A1 | 0 | 50 | 0 | 0 | 0 | 0 | 0 |
| Amino fluid A3 | 65 | 15 | 25 | 15 | 0 | 0 | 0 |
| Amino fluid A4 | 0 | 0 | 40 | 50 | 65 | 40 | 65 |
| Amino fluid A5 | 0 | 0 | 0 | 0 | 0 | 25 | 0 |
| TERGITOL TMN-6 | 40 | 40 | 40 | 40 | 40 | 40 | 40 |
| Part I Water | 65 | 65 | 65 | 65 | 65 | 65 | 220 |
| Acetic Acid | 1 | 1 | 1 | 1 | 1 | 1 | 1 |
| Part II Water | 155 | 155 | 155 | 155 | 155 | 155 | 0 |
| Haze | 200+ | 100 | 80 | 50 | 40 | 60 | 60 |
| pH | 5.5 | 5.5 | 5.5 | 5.5 | 5.5 | 5.5 | 5.5 |

A3 = linear, trimethylsilylterminated, —$(CH_2)_3$—$NH$—$CH_2$—$CH_2$—$NH_2$ viscosity = 400 centistokes, amine content of 0.07 meq./gr.
A4 = linear, trimethylsilylterminated, —$(CH_2)_3$—$NH$—$CH_2$—$CH_2$—$NH_2$ viscosity = 4500–5000 centistokes, amine content of 0.12 meq./gr.
A5 = linear, trimethylsilylterminated, —$(CH_2)_3$—$NH$—$CH_2$—$CH_2$—$NH_2$ viscosity = 4500–5000 centistokes, amine content of 0.07 meq./gr.

Example 25

While warming to 70 C, 20 parts of an aminofunctional silicone (linear, trimethylsilyl terminated, —$(CH_2)_3$—$NH$—$CH_2$—$CH_2$—$NH_2$ pendant, viscosity of 270,000 centistokes, amine content of 0.6 meq/gr.) was mixed with 12.5 parts of TERGITOL TMN-6. Part I water (20 parts) was then added dropwise at 70C. After water addition was complete, 0.5 parts of acetic acid was added. The mixture rapidly thickened and became translucent Part II water (47 parts) was then added rapidly with good agitation. A microemulsion having an ASTM haze number of about 40 was obtained. Upon heat aging for two weeks at 50 C, the haze increased to 50.

Example 26

This example shows the effect of adding a buffer to the emulsion formulation.

While warming to 70 C, 20 parts of an aminofunctional silicone (linear, trimethylsilyl terminated, —$(CH_2)_3$—$NH$—

$CH_2$—$CH_2$—$NH_2$ pendant, viscosity of 270,000 centistokes, amine content of 0,6 meq/gr.) was mixed with 12.5 parts of TERGITOL TMN-6. Part I water (20 parts) was then added dropwise at 70C. After water addition was complete, a solution of 2 parts of water, 0.5 parts of acetic acid and 0.25 parts of sodium acetate was added. The mixture rapidly thickened and became translucent Part II water (44.75) parts) was then added rapidly with good agitation. A microemulsion having an ASTM haze number of about 10 was obtained. Upon heat aging for two weeks at 50 C, the haze increased to 40.

Example 27

This example shows the effect of varying the amount of Part I water.

While warming to 70 C, 20 parts of an aminofunctional silicone (linear, trimethylsilyl terminated, —$(CH_2)_3$—NH—$CH_2$—$CH_2$—$NH_2$, viscosity of 270,000 centistokes, amine content of 0.6 meq/gr.) was mixed with 12.5 parts of TERGITOL TMN-6. Part I water (24 parts) was then added dropwise at 70C. After water addition was complete, 0.5 parts of acetic acid was added. The mixture rapidly thickened and became translucent This mixture was thinner than that obtained in example 1 and was much easier to work with. Part II water (47 parts) was then added rapidly with good agitation. A microemulsion having an ASTM haze number of under 10 was obtained. Upon heat aging for two weeks at 50 C, the haze increased to 40.

Example 28

This example shows the effect of varying the amount of Part I water.

While warming to 70 C, 20 parts of an aminofunctional silicone (linear, trimethylsilyl terminated, —$(CH_2)_3$—NH—$CH_2$—$CH_2$—$NH_2$ pendant, viscosity of 270,000 centistokes, amine content of 0.6 meq/gr.) was mixed with 12.5 parts of TERGITOL TMN-6. Part I water (10 parts) was then added dropwise at 70C. After water addition was complete, 0.5 parts of acetic acid was added. The mixture rapidly thickened and became translucent. The emulsion was too thick to stir easily with an overhead stirrer. Part II water (57 parts) was then added rapidly with good agitation. A microemulsion having an ASTM haze number of about 20 was obtained. Upon heat aging for two weeks at 50 C, the emulsion separated into two layers.

Example 29

This example shows the effect of using a surfactant blend.

While warming to 70 C, 20 parts of an aminofunctional silicone (linear, trimethylsilyl terminated, —$(CH_2)_3$—$NHCH_2$—$CH_2$—$NH_2$ pendant, viscosity of 270,000 centistokes, amine content of 0.6 meq/gr.) was mixed with 9 parts of TERGITOL TMN-6 and 3 parts of TRITON X-405. Part I water (24 parts) was then added dropwise at 70C. After water addition was complete, 0.5 parts of acetic acid was added. The mixture rapidly thickened and became translucent. Part II water (43.5 parts) was then added rapidly with good agitation. A microemulsion having an ASTM haze number of about 50 was obtained. Upon heat aging for two weeks at 50 C, the haze increase to 100.

Example 30

This example shows the effect of using a surfactant blend.

While warming to 70 C, 20 parts of an aminofunctional silicone (linear, trimethylsilyl terminated, —$(CH_2)_3$—NH—$CH_2CH_2$—$NH_2$ pendant, viscosity of 270,000 centistokes, amine content of 0.6 meq/gr.) was mixed with 11 parts of TERGITOL TMN-6 and 2.5 parts of TRITON X-405. Part I water (24 parts) was then added dropwise at 70C. After water addition was complete, 0.5 parts of acetic acid was added. The mixture rapidly thickened and became translucent Part II water (43.5 parts) was then added rapidly with good agitation. A microemulsion having an ASTM haze number of under 10 was obtained. Upon heat aging for two weeks at 50 C, the haze did not noticeably increase.

Example 31

This example shows the effect of using a surfactant blend.

While warming to 70 C, 20 parts of an aminofunctional silicone (linear, trimethylsilyl terminated, —$(CH_2)_3$—NH—$CH_2CH_2$—$NH_2$, viscosity of 270,000 centistokes, amine content of 0.6 meq/gr.) was mixed with 8.5 parts of TERGITOL TMN-6 and 1.5 parts of TRITON X405. Parts 1 water (24 parts) was then added dropwise at 70C. After water addition was complete, 0.5 parts of acetic acid was added. The mixture rapidly thickened and became translucent Part II water (43.5 parts) was then added rapidly with good agitation. An emulsion having an ASTM haze number of greater than 100 was obtained. The emulsion separated upon heat aging at 50 C.

Example 32

This example shows the effect of varying the aminofunctional silicone.

While warming to 70 C, 20 parts of an aminofunctional silicone (linear, trimethylsilyl terminated, —$(CH_2)_3$—NH—$CH_2$—$NH_2$, viscosity of 140,000 centistokes, amine content of 0.3 meq/gr.) was mixed with 12.5 parts of TERGITOL TMN6. Part I water (20 parts) was then added dropwise at 70C. After water addition was complete, 0.5 parts of acetic acid was added. The mixture rapidly thickened and became translucent Part II water (47 parts) was then added rapidly with good agitation. A microemulsion having an ASTM haze number of about 10 was obtained. Upon heat aging for two weeks at 50 C, the emulsion separated into two layers.

Example 33

This example shows the effect of using a different fluid. While warming to 70 C, 20 parts of an aminofunctional silicone (linear, trimethylsilyl terminated, —$(CH_2)_3$—NH—$CH_2$—$CH_2$—$NH_2$ pendant, viscosity of 140,000 centistokes, amine content of 0.3 meq/gr.) was mixed with 11 parts of TERGITOL TMN-6 and 2.5 parts of TRITON X405. Part I water (24 parts) was then added dropwise at 70C. After water addition was complete, 0.5 parts of acetic acid was added. The mixture rapidly thickened and became translucent Part II water (43.5 parts) was then added rapidly with good agitation. A microemulsion having an ASTM haze number of under 10 was obtained. Upon heat aging for two weeks at 50 C, the haze did not noticeably increase.

Examples 34 through 38

Examples 34 through 38 were prepared by the technique described in example 25. A summary of the results obtained on the preparations exemplified by examples 34 through 38 is presented in the following Table:

|  | EX34 | EX35 | EX36 | EX7 | EX38 |
|---|---|---|---|---|---|
| FLUID A | 20 | 20 | 0 | 0 | 0 |
| FLUID B | 0 | 0 | 20 | 20 | 0 |
| FLUID C | 0 | 0 | 0 | 0 | 20 |
| PRIMARY SURFACTANT[a] | 12.5 | 8.5 | 12.5 | 8.5 | 12.5 |
| SECONDARY SURFACTANT[b] | 0 | 2.5 | 0 | 2.5 | 0 |
| PART I WATER | 25 | 25 | 25 | 25 | 25 |
| BUFFER | 3.7 | 3.7 | 3.0 | 3.0 | 2.5 |
| PART II WATER | 38.8 | 40.3 | 39.5 | 41 | 40 |
| INITIAL HAZE | 20 | 20 | 30 | 30 | 40 |
| AGING HAZE | 40 | 20 | 50 | 40 | >100 |

Fluid A = linear, trimethylsilyl terminated, —$(CH_2)_3$—NH—$CH_2$—$CH_2$—$NH_2$, viscosity of 2,000,000 centistokes, amine content of 0.6 meq/gr.
Fluid B = linear, trimethylsilyl terminated, —$(CH_2)_3$—NH—$CH_2$—$CH_2$—$NH_2$, viscosity of 1,5000,000 csk, amine content of 0.3 meq/gr.
Fluid C = linear, trimethylsilyl terminated, —$(CH_2)_3$—NH—$CH_2$—$CH_2$—$NH_2$, viscosity of 800,000 csk, amine content of 0.15 meq/gr.
Primary surfactant = Tergitol TMN-6 from Union Carbide
Secondary surfactant = Triton X-405 from Union Carbide
Buffer solution is 3 parts water, 0.5 parts acetic acid and 0.2 parts sodium acetate.
Aging run in a 50 C. oven for 3 weeks in a closed top container under nitrogen.

Examples 39 through 43: Personal Care Product Formulations

The personal care products exemplified by examples 39 through 43 were prepared using microemulsions prepared by the process of the present invention using a linear trimethylsilyl terminated amino functional silicone; the microemulsions had a silicone content of 20 weight percent. Examples 39 and 40 utilized a microemulsion comprising a silicone fluid having a viscosity of 150 centistokes at 25° C. and an amino content of 0.55 meq./gr. Examples 41 through 43 utilized a microemulsion comprising a high viscosity amino silicone fluid having a viscosity of 189,000 centistokes at 25° C. and an amino content of 0.30 meq./gr.

Example 39

A clear conditioner was prepared from the following components:

| Material | Amount (wt. %) |
|---|---|
| Deionized water | 88.55 |
| Hydroxyethyl Cellulose | 1.0 |
| Cetrimonium Chloride | 3.5 |
| Silicone microemulsion | 6.0 |
| Glydant Plus ® | 0.2 |
| Fragrance | 0.75 |

The preparative procedure employed was as follows:
With good stirring the hydroxyethyl cellulose was added to the deionized water. When complete dispersion was achieved, the Glydant Plus® was added and stirred until the mixture was again clear. The aqueous mixture was heated to 60° C. When the mixture was clear, the Cetrimonium chloride and the silicone microemulsion prepared by the process of the present invention were added individually. The mixture was stirred while allowed to cool. When the temperature was below 40° C., the fragrance was added. Stirring was continued for approximately 20 minutes after the addition of the fragrance.

Generally, the optional components may be varied, substituted, or omitted according to the teachings of the art For example, in order to prevent bacterial growth, preservatives may be added. Additionally fragrances, pH adjusting agents, antistatic or softening agents, cationic polymers, thickening agents, nonionic polymers such as acrylic acid polymers, neutralizing materials such as triethanolamine, sunscreens, antioxidants, proteins, vitamins, botanical extracts, and the like may be added.

Example 40

A conditioning or 2 in 1 shampoo was prepared from the following components:

| Material | Amount (wt. %) |
|---|---|
| Deionized water | 33.89 |
| Hydroxyethyl Cellulose | 2.0 |
| Ammonium Lauryl Sulfate (as 26% solution) | 15.38 |
| Ammonium Laureth Sulfate (as 28% solution) | 21.43 |
| Cocamidopropyl Betaine (as a 35% solution) | 11.43 |
| Dowicil 200 ® | 0.2 |
| Silicone microemulsion | 5.0 |
| Citric acid | sufficient to adjust to desired pH |
| Lauramide DEA | 3.5 |
| Cetrimonium Chloride | 6.67 |
| Fragrance | 0.5 |

The preparative procedure employed was as follows:
The hydroxyethyl cellulose was added to the water and stirred until the hydroxyethyl cellulose was thoroughly solvated. The Dowicil 200® was added and the aqueous mixture was stirred and heated to 60° C. The surfactants were added in the order listed, individually, followed by stirring until the mixture gave a homogeneous appearance. The Lauramide DEA was melted and added to the mixture. The mixture was then cooled with stirring continued during the cooling. When the temperature was below 40° C., the silicone microemulsion and fragrance were individually added followed by stirring. Mixing was continued for approximately 20 minutes after the addition of the last component.

Example 41

A clear conditioning shampoo formulation was prepared from the following components:

| Material | Weight Percent |
|---|---|
| Deionized water | 31.32 |
| Ammonium Lauryl Sulfate (26% sol'n.) | 24.00 |
| Ammonium Laureth Sulfate (28% sol'n.) | 14.30 |
| Cocamidopropyl Betaine (35% sol'n.) | 11.43 |
| Amino Silicone Gum Microemulsion | 7.0 |
| Cocamide MEA | 2.5 |
| Polysorbate 80 | 2.5 |
| Lauramide DEA | 2.0 |
| Glycerin | 2.0 |
| Dimethicone Copolyol | 1.0 |
| Guar Hydroxypropyltrimonium Chloride | 0.75 |

-continued

| Material | Weight Percent |
|---|---|
| Fragrance | 0.75 |
| FD&C Yellow #5 (1.0% sol'n.) | 0.25 |
| Methyl Paraben | 0.15 |
| Propyl Paraben | 0.05 |

The methyl and propyl parabens were dissolved in water. The guar hydroxypropyltrimonium chloride was added slowly to the water solution with good stirring. When the guar compound was thoroughly solvated, the ammonium lauryl sulfate, the ammonium laureth sulfate, and the cocamidopropyl betaine were added individually in order. The solution was heated to 65° C. The lauramide DEA and the cocamide MEA were melted together and added to the hot solution with good mixing. The heat was discontinued. The polysorbate 80, glycerin, silicone fluid, and color, and fragrance as desired were mixed together and added to the solution after the temperature had cooled to below 45° C. Stirring was continued for an additional 10–15 minutes, followed by addition of the silicone gum microemulsion. After addition of the silicone gum microemulsion stirring was continued for an additional 15 minutes.

Example 42

A hair conditioner formulation was prepared from the following components:

| Material | Weight Percent |
|---|---|
| Deionized water | 73.40 |
| Silicone Gum Microemulsion | 10.00 |
| Cyclomethicone | 5.00 |
| Behentrimonium Methosulfate and Cetearyl Alcohol | 2.75 |
| Glycerin | 2.50 |
| Dimethicone Copolyol | 1.75 |
| Stearamidopropyldimethyl amine | 1.50 |
| Cetyl Alcohol | 1.50 |
| Pentaerythritol Tefrastearate | 1.30 |
| Methyl Paraben | 0.20 |
| Propyl paraben | 0.10 |
| Fragrance | as desired |

The methyl and propyl parabens were dissolved in water. The solution was heated to 65° C. The behentrimonium methosulfate (and) cetearyl alcohol, stearamidopropyldimethyl amine, and pentaerythritol tetrastearate were melted together and added to the solution with good stirring. The solution was allowed to cool. The glycerin and the dimethicone copolyol were mixed together along with optional fragrance and added to the solution after the temperature had dropped below 45° C., with continued stirring for 15–20 minutes. The silicone gum microemulsion was added with stirring for an additional 10–15 minutes. The cyclomethicone was added with stirring for an additional 10 minutes.

Example 43

A hair conditioning styling mousse was prepared from the following components:

| Material | Weight Percent |
|---|---|
| Deionized water | 79.45 |
| Polyquaternium 11 | 5.80 |
| Oleth-20 | 0.75 |
| Silicone Gum Microemulsion | 1.50 |
| Dimethicone Copolyol | 0.50 |
| Propellant hydrocarbons | 12.00 |

The water was heated to 45° C., the polyquaternium 11 was added, and the solution stirred until completely dissolved. The Oleth-20 was then added with continued stirring until complete dissolution was obtained. The solution was then cooled below 45° C. and the silicone gum microemulsion and dimethicone copolyol were added. Stirring was continued until the solution was cool. The liquid mousse preparation was then loaded into a pressurizable container and pressurized with a mixture of light hydrocarbons.

The foregoing examples describe generally the preparation and uses of microemulsions prepared from a single amino silicone fluid. The viscosity of the amino silicone fluid may vary widely. The following examples describe the incorporation of MQ resins with an amino functional silicone fluid and the subsequent microemulsification of the mixture of the MQ resin and the amino functional silicone, and the uses thereof in personal care compositions.

Example 44

Emulsification of MQ amino functional silicone resin blends, general procedure:

1) blend an MQ resin A(2) with an amino functional silicone A(1),
2) add surfactants, A(3), preferably a branched secondary alcohol ethoxylate, and preferably in a ratio of 1.0:0.625 (oil/resin mix to surfactant by weight),
3) blend at 70–75° C.,
4) slowly add part I water with stirring in an amount equal to the amount of oil while maintaining the temperature at 70° C.,
5) add acid to adjust pH, preferably acetic acid,
6) add the part II water rapidly, the water may contain additional soluble components such as biocides and other additives.

Example 45

Personal care product utilizing a microemulsified MQ amino functional silicone blend. A solution of a methyl MQ resin, 50% by weight in cyclomethicone was microemulsified with an amino silicone fluid, trimethylsilylamodimethicone having an amino content of 0.8 meq/g; the weight ratio of the mixture of silicones was 50% amino silicone fluid and 50% of the MQ solution in cyclomethicone. This microemulsion was utilized to prepare a conditioning curl refresher having the following composition:

| Material | Wt. % |
|---|---|
| Deionized Water | 89.99 |
| Polyquaternium-11 | 0.67 |
| Aminomethyl Propanol | 0.03 |
| Polysorbate-80 | 0.60 |
| Dimethicone Copolyol | 0.50 |
| Microemulsion Mixture | 5.00 |
| Glycerin | 2.50 |
| Citric Acid | 0.01 |
| Methyl Paraben | 0.15 |
| Propyl Paraben | 0.05 |
| Fragrance | 0.50 |

Example 46

Personal care product utilizing a microemulsified MQ amino functional silicone blend. A solution of a methyl MQ, 50% by weight in cyclomethicone was microemulsified with an amino silicone fluid, trimethylsilylamodimethicone having an amino content of 0.8 meq/g; the weight ratio of the mixture of silicones was 50% amino silicone fluid and 50% of the MQ solution in cyclomethicone. This microemulsion was utilized to prepare a skin care product having the following composition:

| Material | Wt. % |
|---|---|
| Deionized Water | 79.90 |
| Cetyl alcohol | 2.00 |
| Glyceryl Stearate & PEG-100 Stearate | 2.50 |
| Acetylated Lanolin Alcohol | 2.00 |
| Dimethicone | 3.00 |
| Microemulsion Mixture | 8.00 |
| Magnesium aluminum silicate | 1.50 |
| Fragrance | 0.50 |
| Propyl paraben | 0.10 |
| Butyl paraben | 0.15 |
| Methyl paraben | 0.15 |
| Phenoxyethanol | 0.20 |

Generally, the optional components in personal care products may be varied, substituted, or omitted according to the teachings of the art For example, in order to prevent bacterial growth, preservatives may be added. Additionally fragrances, pH adjusting agents, antistatic or softening agents, cationic polymers, thickening agents, nonionic polymers such as acrylic acid polymers, neutralizing materials such as triethanolamine, sunscreens, antioxidants, proteins, vitamins, botanical extracts, and the like may be added.

Example 47 Preparation of an MQ Microemulsion

To 15 parts by weight of an amino functional silicone (linear, trimethylsilyl terminated, —$(CH_2)_3$—NH—$CH_2$—$NH_2$ pendant, viscosity of 1,500 to 2,500 csk, amine content of 0.8 meq/gr) was mixed 5 parts by weight of 1:1 weight mixture of MQ resin/volatile silicone ($D_5$) blend and 12 parts by weight of Tergitol TMN-6 ®. The mixture was heated to 65° C. Water, 20 parts by weight, was then added slowly with good agitation while heating to 70° C. After the addition of water was completed, 0.5 parts by weight of acetic acid was added. The mixture thickened and became substantially transparent After stirring for 2–5 minutes at 70° C., 47.5 parts by weight of Part II water was rapidly added with good agitation. Upon cooling a microemulsion having an ASTM haze number of 20 was obtained.

These examples illustrate the types of fluids and resins that form microemulsions:

| Component | Exp. 48 | Exp. 49 | Exp. 50 | Exp. 51 | Exp. 52 | Exp. 53 | Exp. 54 | Exp. 55 | Exp. 56 |
|---|---|---|---|---|---|---|---|---|---|
| Parts by wt. per 100 parts by weight | | | | | | | | | |
| Fluid A1 | 15 | 15 | 15 | 10 | 10 | 0 | 0 | 0 | 0 |
| Fluid A2 | 0 | 0 | 0 | 0 | 0 | 15 | 15 | 12.5 | 10 |
| Resin R1 | 5 | 0 | 0 | 10 | 0 | 5 | 0 | 0 | 10 |
| Resin R2 | 0 | 5 | 0 | 0 | 10 | 0 | 5 | 7.5 | 0 |
| Resin R3 | 0 | 0 | 5 | 0 | 0 | 0 | 0 | 0 | |
| TMN-6 Part I | 12 | 12 | 12 | 12 | 12 | 12 | 12 | 12 | 12 |
| Water Acetic Acid Part II | 20 0.5 | 20 0.5 | 20 0.5 | 20 0.5 | 20 0.5 | 20 0.5 | 20 0.5 | 20 0.5 | 20 0.5 |
| Water ASTM | 47.5 | 47.5 | 47.5 | 47.5 | 47.5 | 47.5 | 47.5 | 47.5 | 47.5 |
| Haze | 10 | 10 | 10 | 20 | 20 | 10 | 20 | 20 | 200+ |

| Component | Exp. 57 | Exp. 58 | Exp. 59 | Exp. 60 | Exp. 61 | Exp. 62 | Exp. 63 | Exp. 64 | Exp. 65 |
|---|---|---|---|---|---|---|---|---|---|
| Parts by wt. per 100 parts by weight | | | | | | | | | |
| Fluid A2 | 0 | 0 | 0 | 0 | 0 | 0 | 15 | 15 | 15 |
| Fluid A3 | 15 | 15 | 0 | 0 | 0 | 0 | 0 | 0 | 0 |
| Fluid A4 | 0 | 0 | 17.5 | 17.5 | 0 | 0 | 0 | 0 | 0 |
| Fluid A5 | 0 | 0 | 0 | 0 | 15 | 17.5 | 0 | 0 | 0 |
| Resin R1 | 5 | 0 | 2.5 | 5 | 0 | 2.5 | 0 | 0 | 0 |
| Resin R2 | 0 | 5 | 0 | 0 | 5 | 0 | 5 | 5 | 0 |
| Resin R3 | 0 | 0 | 0 | 0 | 0 | 0 | 0 | 0 | 5 |
| TMN-6 | 12 | 12 | 12 | 12 | 12 | 12 | 0 | 0 | 12 |
| 15-S-9 ® | 0 | 0 | 0 | 0 | 0 | 0 | 12 | 0 | 0 |
| Minfoam-1X ® Part I | 0 | 0 | 0 | 0 | 0 | 0 | 0 | 12 | 0 |
| Water Acetic Acid Part II | 20 0.5 | 20 0.5 | 20 0.5 | 20 0.5 | 20 0.5 | 20 0.5 | 20 0.5 | 20 0.5 | 20 0.5 |
| Water ASTM | 47.5 | 47.5 | 47.5 | 47.5 | 47.5 | 47.5 | 47.5 | 47.5 | 47.5 |
| Haze | 20 | 20 | 60 | 100+ | 200+ | 200+ | 20 | 200+ | 20 |

| Component | Exp. 66 | Exp. 67 | Exp. 68 | Exp. 69 | Exp. 70 | Exp. 71 | Exp. 72 | Exp. 73 | Exp. 74 |
|---|---|---|---|---|---|---|---|---|---|

| Parts by wt. per 100 parts by weight | | | | | | | | | |
|---|---|---|---|---|---|---|---|---|---|
| Fluid A1 | 17.5 | 0 | 15 | 15 | 17.5 | 17.5 | 0 | 0 | 17.5 |
| Fluid A2 | 0 | 17.5 | 0 | 0 | 0 | 0 | 17.5 | 17.5 | 0 |
| Resin R4 | 2.5 | 2.5 | 0 | 0 | 2.5 | 0 | 0 | 0 | 0 |
| Resin R5 | 0 | 0 | 5 | 0 | 0 | 0 | 0 | 0 | 0 |
| Resin R6 | 0 | 0 | 0 | 5 | 0 | 0 | 0 | 0 | 0 |
| Resin R7 | 0 | 0 | 0 | 0 | 0 | 2.5 | 2.5 | 0 | 0 |
| Resin R8 | 0 | 0 | 0 | 0 | 0 | 0 | 0 | 2.5 | 2.5 |
| TMN-6 Part I | 12 | 12 | 12 | 12 | 12 | 12 | 12 | 12 | 12 |
| Water | 20 | 20 | 20 | 20 | 20 | 20 | 20 | 20 | 20 |
| Acetic Acid Part II | 0.5 | 0.5 | 0.5 | 0.5 | 0.5 | 0.5 | 0.5 | 0.5 | 0.5 |
| Water | 47.5 | 47.5 | 47.5 | 47.5 | 47.5 | 47.5 | 47.5 | 47.5 | 47.5 |
| ASTM Haze | 200+ | 200+ | 200+ | 200+ | 200+ | 200+ | 200+ | 200+ | 200+ |

Fluid A1 is a linear, trimethylsilyl terminated, —$(CH_2)_3$—NH—$(CH_2)_2$—$NH_2$ pendant, viscosity of 1,500 to 2,500 csk, amine content of 0.8 meq/gr silicone.
Fluid A2 is a branched, trimethylsilyl terminated, —$(CH_2)_3$—NH—$(CH_2)_2$—$NH_2$ pendant, viscosity of 150 to 300 csk, amine content of 0.53 meq/gr silicone.
Fluid A3 is a linear, trimethylsilyl terminated, —$(CH_2)_3$—NH—$(CH_2)_2$—$NH_2$ pendant, viscosity of 60,000 csk, amine content of 0.3 meq/gr silicone.
Fluid A4 is a branched, trimethylsilyl terminated, —$(CH_2)_3$—NH—$(CH_2)_2$—NH2 pendant, viscosity of 150 to 300 csk, amine content of 0.15 meq/gr silicone.
Fluid A5 is a branched, trimethoxy terminated, —$(CH_2)_3$—NH—$(CH_2)_2$—$NH_2$ pendant, viscosity of 10 to 40 csk, amine content of 0.45 meq/gr silicone.
Resin R1 is a 1:1 weight mixture of a volatile silicone ($D_5$) and MQ methyl resin, M/Q ratio=0.76.
Resin R2 is a 1:1 weight mixture of a polydimethylsiloxane and MQ methyl resin, M/Q ratio=0.76.
Resin R3 is a dried version of Resin R1, 100% silicone solids.
Resin R4 is a TD resin with a phenyl to methyl ratio of about 1:1, about 85% solids in naphthalene.
Resin R5 is a TD resin with a phenyl to methyl ratio of about 1:1, about 50% solids in toluene.
Resin R6 is TD resin with a phenyl to methyl ratio of 2:3, about 80% solids in toluene isopropyl alcohol solvent mixture.
Resin R7 is a TD methyl resin, 100% silicone solids with a viscosity of 200–700 csk.
Resin R8 is a TD methyl resin, 100% silicone solids, T/D ratio=about 49:1.
15-S9® is an ethoxylated secondary alcohol surfactant available commercially from Union Carbide Corporation.
Minfoam-1X® is a blend of surfactants comprising ethoxylated secondary alcohols available from Union carbide Corporation.

While one of the benefits of using the microemulsions prepared by the process of the present invention is the ability to prepare clear personal care products having an ASTM haze number below about 100 to 150, opacifying or pearlizing agents may be incorporated into the personal care product formulations if desired, as demonstrated in example 42. The microemulsions prepared by the process of the present invention provide conditioning benefits to a variety of personal care products including, but not limited to, hair coloring compositions, rinses, neutralizing lotions, creams, gels, mousses, aerosols, and pump sprays.

It is apparent from the foregoing that many other variations and modifications may be made in the compositions and methods herein before described without deviating substantially from the process and compositions of the present invention. Accordingly, the embodiments of the present invention herein before described are exemplary only and are not intended to limit in any fashion or manner the scope of the claims appended hereto.

What is claimed is:

1. A process for preparing a transparent microemulsion comprising:
  (a) preparing a blend comprising a low amino content silicone and an MQ resin wherein said low amino content microemulsifiable silicone has the formula:

$M(R_aQ_bSiO_{(4-a-b)/2})_x(R_cSiO_{(4-c)/2})_yM$ wherein R is a hydrocarbon or hydrocarbon radical having from 1 to about 6 carbon atoms, Q is a polar radical having the general formula —$R^1HZ$, wherein $R^1$ is a divalent linking group bound to hydrogen and a radical Z wherein $R^1$ is comprised of carbon and hydrogen atoms; carbon, hydrogen and oxygen atoms, or carbon, hydrogen and nitrogen atoms; and Z is an amino containing radical having the formula:

—$N(CH_2)_z(CH_2)_{zz}NH$ wherein z is one or greater and zz is zero or greater subject to the limitation such that when zz is zero Z has the formula:

—$NH(CH_2)_zNH_2$ wherein z is one or greater; a ranges from about 0 to about 2, b ranges from about 1 to about 3 such that a+b is less than or equal to 3, and c is a number in the range of from about 1 to about 3; and x is a number in the range of from 5 to about 2,000, and y is a number in the range of from about 800 to about 10,000, and M is a silicone endstopping group; and wherein said MQ resin has the formula:

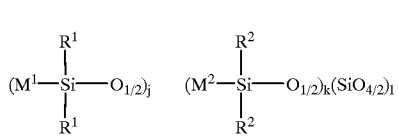

where both $R^1$ and $R^2$ are independently selected from the group consisting of alkyl hydrocarbon radicals having from 1 to 12 carbon atoms, and both $M^1$ and $M^2$ are independently selected from the group consisting of phenyl, phenethyl, polyether, hydrogen, and alkyl hydrocarbon radicals having from 1 to 23 carbon atoms in any combination subject to the limitation that the ratio of the subscripts j, k, and l satisfies the following relationship:

$0.5 \leq (j+k)/l \leq 4.0$.

(b) adding a surfactant having a phase inversion temperature ranging from about 45 to 0° C. about 95° C. to said blend;

(c) heating said blend and said surfactant to a temperature ranging from about 45° C. to 95° C. said temperature being below the phase inversion temperature of said surfactant;

(d) adding part I water;

(e) adding an acid; and (f) adding part II water said microemulsion being cooled whereby said microemulsion has an ASTM D871 haze below about 150 and a mean particle size ranging from about 0.005 microns to about 0.050 microns.

2. The method of claim 1 wherein steps (d) and (e) are performed substantially simultaneously.

3. The method of claim 1 wherein the acid of step (e) is dissolved in the water of step (d) to produce an acid solution and said acid solution is added to the mixture of (a) and (b).

4. The method of claim 1 wherein the amount of silicone ranges from 1 to 40 parts per hundred of the total composition of the microemulsion.

5. The method of claim 1 wherein the amount of surfactant ranges from about 1 to 20 parts per hundred of the total composition of the microemulsion.

6. The method of claim 5 wherein the phase inversion temperature of said surfactant ranges from about 55° C. to about 90° C.

7. The method of claim 1 wherein the amount of part I water by weight is substantially equal to the weight of said silicone.

8. The method of claim 1 wherein the amount of part II water by weight ranges from about 40 to about 90 parts per hundred of the total composition of the microemulsion.

9. The method of claim 1 wherein the acid is selected from the group consisting of acetic, hydrochloric, hypophosphorous, lactic, propionic, glycolic, formic, and nitric acids.

10. The method of claim 1 wherein the microemulsifiable silicone has the formula:

$$(CH_3)_3SiO_{xy}Si(CH_3)_3$$

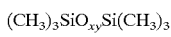

wherein x is a number in the range of from about 5 to about 2,000, and y is a number in the range from about 800 to about 10,000.

11. The method of claim 10 wherein the amino content of said microemulsifiable silicone ranges from about 0.10 meq./gr. to about 10 meq/gr.

12. A translucent oil-in-water microemulsion comprising:

(a) a microemulsifiable amino silicone and an MQ resin, said MQ resin selected from the group of MQ resins having the formula:

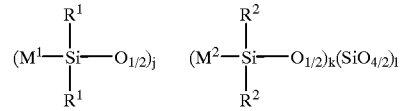

where both $R^1$ and $R^2$ are independently selected from the group of alkyl hydrocarbon radicals having from 1 to 12 carbon atoms, and both $M^1$ and $M^2$ are independently selected from the group of polyether having the formula:

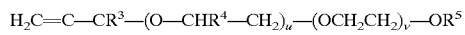

$R^3$ is —$(CH_2)_n$— where n ranges from 1 to about 20, $R^4$ is a one to twenty carbon alkyl group, and $R^5$ is selected from the group consisting of H, —$CH_3$, and —$C(O)CH_3$; and where u and v are integers ranging from 0 to 20 subject to the limitation that $u+v \geq 1$ subject to the limitation that the ratio of the subscripts j, k, and l satisfies the following relationship:

$$0.5 \leq (j+k)/l \leq 4.0.$$

wherein said microemulsifiable amino silicone has a viscosity ranging from 100 to 10,000,000 centistokes at 25° C. and wherein said MQ resin has a viscosity ranging from 50 to 5,000 centistokes at 25° C.; and (b) a surfactant having a phase inversion temperature varying from about 45° C. to about 95° C., and (c) water.

13. A personal care composition comprising the microemulsion of claim 12.

* * * * *